United States Patent [19]

Shiomi et al.

[11] Patent Number: 4,874,888
[45] Date of Patent: Oct. 17, 1989

[54] PROCESS FOR THE PREPARATION OF A DIESTER OF OXALIC ACID

[75] Inventors: Yasushi Shiomi; Tokuo Matsuzaki; Katsuro Masunaga, all of Ube, Japan

[73] Assignee: UBE Industries, Ltd., Yamaguchi, Japan

[21] Appl. No.: 546,532

[22] Filed: Oct. 28, 1983

[30] Foreign Application Priority Data

Nov. 1, 1982 [JP] Japan .................................. 190,855

[51] Int. Cl.$^4$ .............................................. C07C 67/36
[52] U.S. Cl. ..................................... 560/204; 502/74; 502/84; 502/103; 502/171; 502/178; 502/183; 502/184; 502/185; 502/229; 502/258; 502/326; 560/193
[58] Field of Search ................... 560/193, 204; 502/74, 502/84, 103, 171, 178, 184, 185, 229, 258, 326

[56] References Cited

U.S. PATENT DOCUMENTS

| | | | |
|---|---|---|---|
| 3,994,960 | 11/1976 | Yamazaki et al. | 560/204 |
| 4,076,949 | 2/1978 | Zehner | 560/204 |
| 4,229,591 | 10/1980 | Nishimura et al. | 560/193 |
| 4,384,133 | 5/1983 | Miyazaki et al. | 560/204 |
| 4,410,722 | 10/1983 | Miyazaki et al. | 560/204 |

FOREIGN PATENT DOCUMENTS 2025950A 1/1980 United Kingdom .

Primary Examiner—Werren B. Lone
Assistant Examiner—Vera C. Clarke
Attorney, Agent, or Firm—Sherman and Shalloway

[57] ABSTRACT

In a process for preparing a diester of oxalic acid by the vapor phase catlytic reaction of carbon monoxide with an ester of nitrous acid in the presence of a catalyst composed of a solid carrier and a catalyst component supported on the carrier, the improvement wherein said catalyst component is composed of
(a) a platinum-group metal or a salt thereof, and
(b) at least one member selected from the group consisting of iron and an iron (II or III) compound,
the atomic ratio of the component (a) to the component (b) as metal being from 10,000:1 to 1:4.

15 Claims, No Drawings

PROCESS FOR THE PREPARATION OF A DIESTER OF OXALIC ACID

This invention relates to an improved process for preparing a diester of oxalic acid by the vapor (or gaseous) phase catalytic reaction of carbon monoxide with an ester of nitrous acid in the presence of a catalyst composed of a solid carrier and a catalyst component supported on the carrier. According to this process, the diester of oxalic acid can be produced at a higher selectivity and higher yield with a longer catalyst life than a conventional process involving using a platinum-group metal or a salt thereof as the catalyst component while maintaining an excellent space time yield.

More specifically, this invention relates, in the aforesaid vapor phase catalytic reaction, to the improvement which comprises using a catalyst composed of a solid carrier and a catalyst component supported on the carrier, said component being composed of (a) a platinum-group metal or a salt thereof and (b) at least one member selected from the group consisting of iron and an iron (II or III) compound, the atomic ratio of the component (a) to the component (b) as metal being from 10,000:1 to 1:4.

The diester of oxalic acid is a known compound having important utility as a starting material for synthesis of oxalic acid, oxamide, glycols, dyestuff intermediates and medicines.

The process for preparing a diester of oxalic acid by the vapor phase catalytic reaction of carbon monoxide with an ester of nitrous acid in the presence of a catalyst composed of a solid carrier and metallic palladium or a salt thereof supported on the carrier is known (U.S. Pat. No. 4,229,591). This U.S. patent, however, does not at all refer to the use of a co-catalyst component or a catalyst having such a second catalyst component supported together.

Japanese Laid-Open Patent Publication No. 22666/1980 (published on Feb. 18, 1980; corresponding UK Patent Application No. 2025950A) discloses another process for the production of a diester of oxalic acid by a similar vapor phase catalytic reaction to that shown in the above U.S. patent. The Japanese patent document exemplifies palladium, rhodium, iridium, platinum, gold and salts of these metals as ingredients of the catalyst or primary catalytic elements, and iron, copper and salts of these as a carrier which concurrently serves as a catalyst promotor.

The iron or salts thereof in the above proposal are used in very large amounts relative to the primary catalytic elements. Said iron or salts thereof in the above proposal are recognized as carriers, not as cocatalytic elements.

That is, with respect to the amount of iron or its compound, the above proposal describes that the weight ratio of primary catalytic element: iron or its compound (calculated as metals) is 1:100 to 20:80, preferably 1:100 to 5:100 (when the weight ratio is converted into the atomic ratio in the case of the primary catalytic element being palladium, Pd:Fe is 1:about 200 to 1:about 8, preferably 1:about 200 to 1:about 40). Active catalysts exemplified therein are a catalyst composed of $FeCl_2$ and 5% of Pd deposited thereon and a catalyst composed of a metallic iron and 5% of Pd deposited thereon. Moreover, in Examples on a platinum-group metal-iron type catalyst, there are not used common carriers such as silica and alumina. As will be seen from the results of the Comparative Examples described later, when large amounts of iron compounds deviated from the scope of this invention are used relative to the platinum-group metals, the space time yield and selectivity of the diester of oxalic acid decrease drastically.

The present inventors have worked on the improvement of catalysts used in the aforesaid vapor phase catalytic reaction of carbon monoxide with an ester of nitrous acid. In consequence, they have found the following unexpected results. When iron or its compounds are mixed in large amounts with platinum-group metals or salts thereof as desclosed in the above proposal, they do not show a function as a co-catalyst for said reaction but rather hinder the reaction and decrease the yield of the end compound as compared with a case of not mixing them. Despite this fact, when iron or iron (II or III) compounds are mixed in specific amounts, a catalyst life in said reaction is surprisingly much prolonged and a diester of oxalic acid is produced in high yield and high selectivity over a long period of time.

The studies of the present inventors reveal that the aforesaid vapor phase catalyst reaction of carbon monoxide with an ester of nitrous acid is performed in the presence of a solid catalyst composed of a carrier and a catalyst component supported on the carrier, said catalyst component being composed of (a) a platinum-group metal or a salt thereof and (b) iron or an iron (II or III) compound, the atomic ratio of the platinum-group metal:iron being in the range of 10,000:1 to 1:4, with the consequence that the catalyst life in said vapor phase catalytic reaction is markedly prolonged and a diester of oxalic acid can be produced at a high selectivity and high yield over a long period of time.

The use of the solid catalyst in accordance with this invention, compared with the use of a solid catalyst composed of a platinum-group metal or its salt alone, does not decrease a space time yield and selectivity of a diester of oxalic acid in the initiation of the reaction, little decreases said space time yield and selectivity even in the long-term reaction. This means that the catalyst life is remarkably prolonged and the diester of oxalic acid can be produced stably in good yield for a long period of time.

It is an object of this invention therefore to provide an improved process for producing a diester of oxalic acid by vapor-phase catalytic reaction using a specified catalyst.

The above and other objects of this invention along with its advantages will become more apparent from the following description.

Examples of the platinum-group metal used as the catalyst component (a) in this invention are palladium, platinum, rhodium, ruthenium and iridium. They may be used as a mixture of two or more. Palladium, either alone or in combination with another platinum-group metal, is preferred. Examples of the salt of the platinum-group meal include inorganic salts such as nitrates, sulfates, phosphates and halides; organic salts such as acetates, oxalates and benzoates of the above-exemplified metals.

Examples of the iron or iron (II or III) compound used as the catalyst component (b) in this invention are a metallic iron, ferrous sulfate, ferric sulfate, ferrous nitrate, ferric nitrate, ferrous chloride, ferric chloride, ammonium ferrous sulfate, ammonium ferric sulfate, ferrous citrate, ferrous lactate, ferric lactate, ferrous oxide, ferric oxide, tri-iron tetroxide, ferrous hydroxide, ferric hydroxide, and so forth. They may be used as a mixture of two or more.

The ratio of the component (a) to the component (b) may be properly selected. Preferably, the atomic ratio of the component (a) to the component (b), as metal, is from 10,000:1 to 1:4, preferably from 5,000:1 to 1:3. If the amount of the component (b) is too small as compared with the compound (a), the effect of prolonging the life of the catalyst is reduced. If it is too large, the reaction is drastically hindered, and the space time yield and selectivity of the diester of oxalic acid are vastly decreased. Accordingly, the ratio within the above-exemplified range is advantageously used.

This is also clear from the following. For instance, in Examples to be described later, a diester of oxalic acid is provided in a markedly high space time yield. However, the final compound is obtained only in a space time yield of 5 g/liter.hr with an Fe/Pd atomic ratio=5 as in Comparative Example 2 to be described later, in a space time yield of 88 g/liter.hr with an Fe/Pd atomic ratio=10 as in Comparative Example 3, in a space time yield of 76.7 g/kg.hr iwth an Fe/Pd atomic ratio=38 as in Example 6 described in Japanese Laid-Open Patent Publication No. 22666/80 and in a space time yield of 6.7 g/kg.hr with an Fe/Pd atomic ratio=17 as in Example 7 of the same Publication.

In this invention, both the components (a) and (b) are supported on the solid carrier. Examples of the carrier used include activated carbon, alumina (such as $\alpha$-alumina or $\gamma$-alumina), silica, diatomaceous earth, silicon carbide, pumice, zeolite and molecular sieves. Among these, $\alpha$-alumina, $\gamma$-alumina, silica, and silicon carbide are especially preferred.

The amount of the component (a) supported on the solid carrier is preferably about 0.01 to about 10% by weight, more preferably about 0.1 to about 2% by weight, as a platinum-group metal based on the weight of the solid carrier.

There is no restriction on the manner of supporting the catalytic metal components on the solid carrier, and any known means of supporting can be used. Preferably, however, the catalyst is prepared by impregnating a solid carrier with an aqueous solution of a water-soluble salt of a platinum-group metal and an aqueous solution of a water-soluble salt of iron, treating the impregnated solid carrier with an alkali, and then treating the alkali-treated product with a reducing agent in the liquid or gaseous phase.

Alternatively, the above procedure may be carried out by first impregnating the solid carrier with the aqueous solution of a water-soluble salt of a platinum-group metal, treating the impregnated solid carrier with an alkali, dipping the alkali-treated product in the aqueous solution of a water-soluble salt of iron, and then treating the resulting product with a reducing agent in the liquid or gaseous phase.

The impregnation may be effected by dipping the solid carrier in an aqueous solution containing the water-soluble salt of the platinum-group metal and the water-soluble salt of iron, or by dipping the solid carrier in a desired sequence in aqueous solutions of the respective water-soluble salts. As stated above, it is also possible to dip the solid carrier in the aqueous solution containing the water-soluble salt of the platinum-group metal, treat the impregnated solid carrier with an alkali, and then to dip the impregnated carrier in the aqueous solution of the water-soluble salt of iron. The dipping may be performed at a temperature of, for example, about 0° C. to about 90° C. and a period of, for example, about 0.1 to about 10 hours. If desired, the impregnation may also be carried out by spraying the aforesaid aqueous solution onto the solid carrier.

Preferably, the above aqueous solutions are solutions prepared by dissolving the above water-soluble salts in the acidic aqueous solution containing about 0.01 to about 10% by weight of an acidic compound. The use of hte acidic aqueous solution serves to aid in the dissolving of the salt of the platinum-group metal and the salt of iron and to prevent the formation and precipitation of a hydroxide and oxide of the platinum-group metal and iron by hydrolysis. Specific examples of the acidic compound include mineral acids such as hydrochloric acid, nitric acid, sulfuric acid and phosphoric acid and organic acids such as acetic acid. These acidic compounds may, if desired, be used as a mixture of two or more.

The carrier impregnated with the aqueous solutions containing the water-soluble salts is then separated, and if desired washed with water and then dried by, for example, air drying, vacuum drying or heat drying, after which it is subjected to the alkali treatment.

The alkali treatment can be effected by adding the carrier impregnated with the aqueous solutions of the above water-soluble salts to an alkaline aqueous solution containing, for example, about 0.05 to about 10% by weight of an alkaline compound, and stirring the mixture at a temperature of, for example, about 10° to about 90° C. for a period of, for example, about 0.5 to about 10 hours. Examples of the alkaline compound include the hydroxides and salts of alkali metals or alkaline earth metals, for example sodium hydroxide, potassium hydroxide, calcium hydroxide, barium hydroxide, sodium carbonate, sodium hydrogen carbonate and potassium carbonate. If desired, these alkaline compounds may be used as a mixture of two or more in an amount of about 2 to about 40 moles per mole of the sum of the platinum-group metal salt and the iron salt.

After the alkali treatment, the product is optionally washed with water, etc. and dried. The product is then treated with a reducing agent in the liquid or gaseous phase to form the final catalyst.

The liquid-phase reduction is carried out by using such reducing agents as hydrazine, formaldehyde and sodium formate. Specifically, it can be carried out by adding the alkali-treated product to an aqueous solution of the reducing agent in a concentration of about 1 to about 10% by weight, and stirring the mixture at a temperature of, say, about 10° to about 50° C. for a period of, say, about 0.5 to about 10 hours.

The alkaline-treated product may be added directly to the aqueous solution of the reducing agent in performing the reduction. It is more effective, however, to separate the alkali-treated solid product by a solid-liquid separating procedure such as filtration or decantation, wash and dry it, then add the dried product to the aqueous solution of the reducing agent, and subject the dried product to the reducing treatment in the liquid phase.

Examples of reducing agents suitable for use in the gaseous phase reduction are hydrogen, carbon monoxide and ammonia. These reducing agents may be used after being diluted with inert gases such as nitrogen or carbon dioxide. The gaseous phase reduction can be carried out by passing the gaseous reducing agent through the alkali-treated product at a temperature of, for example, about 50° C. to about 800° C. for a period of, say, about 1 to about 10 hours.

The starting gases used in this invention in the reaction of synthesizing the diester of oxalic acid are carbon monoxide and a nitrous acid ester, and sometimes, contain alcohol, nitrogen oxides, etc. as will be stated hereinbelow. In any case, the starting gases contain carbon monoxide effective for the aforesaid vapor phase reducting treatment. Accordingly, as one means of subjecting the aforesaid alkali-treated product to a vapor-phase reducing treatment, there may also be employed a method which comprises feeding the alkali-treated product into an apparatus for the synthesis of the diester of oxalic acid, and prior to the reaction of synthesizing the diester of oxalic acid, subjecting it to a vapor-phase reducing treatment by using a gaseous mixture of carbon monoxide and a nitrous acid ester which may optionally contain alcohol, nitrogen oxides, etc.

According to the process of this invention, carbon monoxide is reacted with an ester of nitrous acid in the vapor phase in the presence of the catalyst prepared as above which is composed of a solid carrier and a catalyst component supported on it, said component being composed of (a) a platinum-group metal or a salt thereof and (b) at least one member selected from iron and an iron (II or III) compound. This reaction can be schematically shown by the following equation.

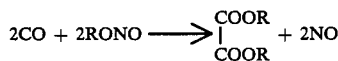

(R=alkyl or cycloalkyl)

As the above scheme shows, this reaction yields nitrogen monoxide equivalent to the consumed nitrous acid ester. Accordingly, the nitrogen monoxide thus formed may be recycled as the starting material for the above reaction by introducing an alcohol and a gas containing molecular oxygen to react them with the nitrogen monoxide as schematically shown below and recovering the resulting nitrous acid ester.

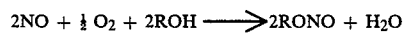

(R=alkyl or cycloalkyl)

An ester of nitrous acid with a saturated monohydric aliphatic alcohol having 1 to 8 carbon atoms or an alicyclic alochol having 1 to 8 carbon atoms is preferred as the ester of nitrous acid. Examples of the aliphatic alcohol are methanol, ethanol, n-propanol, isopropanol, n-butanol, isobutanol, sec-butanol, tert-butanol, n-amyl alcohol, isoamyl alcohol, hexanol and octanol, and examples of the alicyclic alcohol include cyclohexanol and methyl-cyclohexanol. These alcohols may contain a substitutent, such as an alkoxy group, which does not inhibit the reaction.

The reaction is carried out under such conditions that no liquid phase if formed in the reaction zone (namely, in the qaseous or vapor phase). These conditions may vary depending upon the reaction temperature, the reaction pressure, the type and concentration of the nitrous acid ester, etc. Thus, these conditions may be properly selected so that the reaction is carried out in the vapor phase.

The reaction proceeds rapidly even at low temperatures, and side-reactions occurs less as the reaction temperature is lower. It is desirable therefore to perform the reaction at relatively low temperature at which the desired space time yield can be maintained, for example at a temperature of about 50° C. to about 200° C., preferably at about 80° C. to about 150° C. The reaction pressure can also be selected properly. For example, it is atmospheric pressure to about 10 kg/cm$^2$.G, preferably atmospheric pressure to about 5 kg/cm$^2$.G. Pressures below the above-specified lower limit, for example reduced pressures of down to about 200 mmHg, can also be used.

The concentration of the ester of nitrous acid used may be varied over a wide range. To obtain a satisfactory rate of reaction, it is desirable to adjust the concentration of the nitrous acid ester in the starting gaseous mixture introduced into the reactor at 1% by volume or higher, for example about 5 to about 30% by volume.

Carbon monoxide used in the process of this invention may be pure or may be diluted with an inert gas such a nitrogen. The concentration of carbon monoxide in the reaction zone may be varied over a wide range and is, for example, in the range of 10 to 90% by volume.

The catalytic reaction in accordance with this invention may be carried out in a fixed or fluidized bed. The time of contact between the starting gaseous mixture and the catalyst can be properly chosen. For example, the contact time is not more then about 20 seconds, preferably about 0.2 to about 10 seconds.

The nitrous acid ester can be prepared, for example, by reacting an alcohol with a nitrogen oxide in the optional presence of molecular oxygen. The reaction product gas contains the unreacted alcohol and nitrogen oxide (particularly nitrogen monoxide) and at times, traces of water and oxygen in addition to the nitrous acid ester. In the process of this invention, this product gas containing the nitrous acid ester can be used as the starting nitrous acid ester, and good results can be obtained even when such as nitrite containing impurities is used.

The following examples illustrate the practice of the process of the invention in greater detail.

PREPARATION EXAMPLES OF SOLID CATALYST

Palladium chloride (13.33 g) was added to 15.67 g of a 35% by weight aqueous solution of hydrochloric acid, and about 50 cc of water was further added. The mixture was slightly heated to thoroughly dissolve palladium chloride. The resulting mixture was cooled, and water was added to the mixture so that the total amount became 200 g. Said palladium chloride solution (10.14 g) was mixed with a solution of 1.30 g of ferric chloride hexahydrate in 10 cc of water, and water was added to the mixture so that the total weight became 30 cc.

Subsequently, 30 g of spherical α-alumina particles with a particle diameter of 5 mm was dipped in 30 cc of the mixed solution and left to stand for 2 hours while stirring at times. The whole amount of the resulting product was placed on a perforated plate and the mother liquor was completely separated. The alumina particles containing palladium chloride and ferric chloride which were obtained upon separation were dipped in 33 cc of a 1N sodium hydroxide aqueous solution. The solution was stirred at about 60° C. for about 4 hours and subjected to alkali treatment.

The alkali-treated product was collected by filtration and washed with deionized water until a chloride ion was no longer detected with silver nitrate. Subsequently, it was dried in a drier at about 95° C. The resulting product was then placed into a quarts glass tube with an inside diameter of 20 mm set in an electric oven, and subjected to reducing treatment at 500° C. for 3 hours in a hydrogen stream.

Thus, there resulted a spherical solid catalyst (Fe/Pd atomic ratio=1) composed of α-alumina and 0.5% by weight of palladium and 0.262% weight of iron (calculated as metals) deposited thereon.

EXAMPLE 1

A glass reaction tube having an inside diameter of 17 mm and a length of 55 cm was filled with 2 ml (1.8 g) of a catalyst prepared in accordance with said Preparation Example of Solid Catalyst and composed of spherical α-alumina particles with a particle diameter of 5 mm and 0.5% by weight of palladium and 0.262% by weight of iron (calculated as metals) deposited thereon. Glass beads were further filled in the reaction tube and placed on the catalyst layer to a height of 24 cm.

The reaction tube was fixed vertically, and a heated silicone oil was flowed in a jacket portion disposed on the reaction tube, and heating was controlled so that the inside temperature of the catalyst layer become 110° C.

From the top of the reaction tube, a gaseous mixture comprising 20% by volume of carbon monoxide, 15% by volume of methyl nitrite, 15% by volume of methanol, 3% by volume of nitrogen monoxide and 47% by volume of nitrogen was fed at a rate of 20 liters/hr (S.T.P).

The reaction product leaving the reaction tube was first passed through methanol to collect dimethyl oxalate. Low-boiling compounds not collected by methanol were then condensed with dry ice/methanol and collected.

The liquids collected after the initiation of the reaction and after the periods of time elapsed which are shown in Table 1 were analyzed by gas chromatography, and the space time yield (g/liter.hr) of dimethyl oxalate was measured. The results are shown in Table 1.

EXAMPLE 2

The procedure of Example 1 was repeated except using 2 ml of a catalyst prepared in accordance with said Preparation Example of Solid Catalyst and composed of spherical α-alumina particles with a particle diameter of 5 mm and 0.5% by weight of palladium and 0.0262% by weight of iron (calculated as metals) deposited thereon. The results are shown in Table 1.

EXAMPLE 3

The procedure of Example 1 was repeated except using 2 ml of a catalyst prepared in accordance with said Preparation Example of Solid Catalyst and composed of spherical α-alumina particles with a particle diameter of 5 mm and 0.5% by weight of palladium and 0.00262% by weight of iron (calculated as metals) deposited thereon. The results are shown in Table 1.

EXAMPLE 4

The procedure of Example 1 was repeated except using 2 ml of a catalyst prepared in said Preparation Example of Solid Catalyst and composed of spherical α-alumina particles with a particle diameter of 5 mm and 0.5% by weight of palladium and 0.000262% by weight of iron (calculated as metals) deposited thereon. The results are shown in Table 1.

EXAMPLE 5

The procedure of Example 1 was repeated except using 2 ml of a catalyst prepared in accordance with said Preparation Example of Solid Catalyst and composed of spherical α-alumina particles with a particle diameter of 5 mm and 0.5% by weight of palladium and 0.786% by weight of iron (calculated as metals) deposited thereon. The results are shown in Table 1.

COMPARATIVE EXAMPLE 1

A catalyst composed of spherical α-alumina particles with a particle diameter of 5 mm and 0.5% by weight of palladium deposited thereon was produced in accordance with said Preparation Example of Solid Catalyst except that ferric chloride was not added. The procedure of Example 1 was repeated except using 2 ml of said catalyst. The results are shown in Table 1.

COMPARATIVE EXAMPLE 2

The procedure of Example 1 was repeated except using 2 ml of a catalyst prepared in accordance with said Preparation Example of Solid Catalyst and composed of spherical α-alumina particles with a particle diameter of 5 mm and 0.5% by weight of palladium and 1.31% by weight of iron (calculated as metals) deposited thereon. The results are shown in Table 1.

COMPARATIVE EXAMPLE 3

The procedure of Example 1 was repeated except using 2 ml of a catalyst prepared in accordance with said Preparation Example of Solid Catalyst and composed of spherical α-alumina particles with a particle diameter of 5 mm and 0.5% by weight of palladium and 2.62% by weight of iron (calculated as metals) deposited thereon. The results are shown in Table 1.

In Table 1, the space time yield ratio of dimethyl oxalate is the ratio of the space time yield at each elapsed time to that at 8 hours after the initiation of the reaction, the latter being taken as 100 g/liter.hr, and calculated in accordance with the following equation.

$$\text{Ratio of the space time yield of dimethyl oxalate} = \left( \frac{\text{Space time yield of dimethyl oxalate at each reaction time elapsed}}{\text{Space time yield of dimethyl oxalate at 8 hours after the initiation of the reaction}} \right) \times 100$$

TABLE 1

| | | Catalyst | | Reaction temperature (°C.) | Reaction time elapsed (hr) | Space time yield of dimethyl oxalate (g/liter · hr) | Ratio of space time yield of dimethyl oxalate | Selectivity based on CO (%) | | |
|---|---|---|---|---|---|---|---|---|---|---|
| | Pd (wt. %) | Fe (wt. %) | Fe/Pd (atomic ratio) | | | | | Dimethyl oxalate | Dimethyl carbonate | CO$_2$ |
| Example 1 | 0.5 | 0.262 | 1 | 110 | 8 | 1820 | 100 | 97.9 | 1.7 | 0.4 |
| | | | | | 150 | 1800 | 98.9 | 98.3 | 1.2 | 0.4 |

TABLE 1-continued

| | | Catalyst | | Reaction | Reaction time | Space time yield of dimethyl | Ratio of space time yield of | Selectivity based on CO (%) | | |
|---|---|---|---|---|---|---|---|---|---|---|
| | | Pd (wt. %) | Fe (wt. %) | Fe/Pd (atomic ratio) | temperature (°C.) | elapsed (hr) | oxalate (g/liter · hr) | dimethyl oxalate | Dimethyl oxalate | Dimethyl carbonate | $CO_2$ |
| | | | | | | 342 | 1730 | 95.1 | 98.3 | 1.3 | 0.4 |
| | | | | | | 8 | 1612 | 100 | 97.9 | 1.7 | 0.4 |
| | 2 | 0.5 | 0.0262 | 0.1 | 110 | 270 | 1396 | 86.6 | 98.3 | 1.4 | 0.3 |
| | | | | | | 462 | 1329 | 82.4 | 98.4 | 1.3 | 0.3 |
| | | | | | | 8 | 1642 | 100 | 98.5 | 1.3 | 0.2 |
| | 3 | 0.5 | 0.00262 | 0.01 | 110 | 150 | 1437 | 87.5 | 99.3 | 0.5 | 0.2 |
| | | | | | | 318 | 1361 | 82.8 | 98.8 | 1.1 | 0.2 |
| | | | | | | 8 | 1303 | 100 | 98.4 | 1.4 | 0.2 |
| | 4 | 0.5 | 0.00026 | 0.001 | 110 | 150 | 1115 | 85.6 | 98.6 | 1.2 | 0.2 |
| | | | | | | 318 | 1015 | 79.9 | 98.6 | 1.3 | 0.2 |
| | 5 | 0.5 | 0.786 | 3 | 110 | 8 | 1077 | 100 | 98.3 | 1.3 | 0.4 |
| Comparative | | | | | | 8 | 1604 | 100 | 97.8 | 1.7 | 0.5 |
| Example | 1 | 0.5 | 0 | 0 | 110 | 150 | 1295 | 80.7 | 98.3 | 1.2 | 0.5 |
| | | | | | | 318 | 1045 | 65.1 | 97.9 | 1.3 | 0.8 |
| | 2 | 0.5 | 1.31 | 5 | 110 | 8 | 5 | 100 | 63.2 | 14.0 | 22.8 |
| | 3 | 0.5 | 2.62 | 10 | 110 | 8 | 88 | 100 | 6.07 | 15.9 | 23.4 |

COMPARATIVE EXAMPLE 4

A 100-milliliter egg-plant type flask was filled with 9.5 g of ferrous chloride. Then, 40 ml of an aqueous solution containing 2.1% by weight of palladium chloride and 0.84% by weight of hydrochloric acid was added, and the mixture was concentrated to dryness at a temperature of about 50° C. under reduced pressure using a rotary evaporator to obtain a solid. The resulting solid was placed in a Pyrex glass tube with an inside diameter of 20 mm which was set in a tubular electric over to subject it to reducing treatment at a temperature of 200° C. for 2 hours in a hydrogen stream. Thus, there resulted a solid catalyst composed of ferrous chloride and 5% by weight of Pd (calculated as metal) deposited thereon.

The procedure of Example 1 was followed using 2 ml of said catalyst. Though the reaction was continued over 8 hours, the space time yield of dimethyl oxalate was 6 g/liter.hr.

EXAMPLE 6

A catalyst composed of spherical α-alumina particles with a particle diameter of 3 mm and 0.5% by weight of palladium and 0.0262% by weight of iron deposited thereon was produced in accordance with said Preparation Example of Solid Catalyst except that the amount of ferric chloride hexahydrate was changed to 0.130 g and spherical α-alumina particles with a particle diameter of 3 mm were used in place of spherical α-alumina particles with the particle diameter of 5 mm.

The procedure of Example 1 was followed using 2 ml of said catalyst. The results are shown in Table 2.

COMPARATIVE EXAMPLE 5

A catalyst composed of spherical α-alumina particles with a particle diameter of 3 mm and 0.5% by weight of palladium was produced in accordance with said Preparation Example of Solid Catalyst except that ferric chloride hexahydrate was not added and spherical α-alumina particles with a particle diameter of 3 mm were used instead of spherical α-alumina particles with the diameter of 5 mm.

The procedure of Example 1 was followed except using 2 ml of the above catalyst. The results are shown in Table 2.

TABLE 2

| | | Catalyst | | | Reaction | Reaction time | Space time yield of dimethyl | Ratio of* space time yield of | Selectivity based on CO (%) | | |
|---|---|---|---|---|---|---|---|---|---|---|---|
| | | Pd (wt. %) | Fe (wt. %) | Fe/Pd (atomic ratio) | temperature (°C.) | elapsed (hr) | oxalate (g/liter · hr) | dimethyl oxalate | Dimethyl oxalate | Dimethyl carbonate | $CO_2$ |
| Example | | | | | | 126 | 1606 | 100 | 97.9 | 1.4 | 0.7 |
| | 6 | 0.5 | 0.0262 | 0.1 | 110 | 342 | 1623 | 101.1 | 98.3 | 1.0 | 0.7 |
| | | | | | | 630 | 1587 | 98.8 | 98.4 | 1.0 | 0.6 |
| Comparative | | | | | | 54 | 1595 | 100 | 98.8 | 1.1 | 0.1 |
| Example | 5 | 0.5 | 0 | 0 | 110 | 342 | 1331 | 83.4 | 98.9 | 1.1 | ~0 |
| | | | | | | 678 | 1004 | 62.9 | 99.1 | 0.9 | ~0 |

*Said ratio is as defined above.

EXAMPLE 7

A stainless steel reaction tube having an inside diameter of 43 mm and a height of 210 cm was filled with 2.7 liters of a catalyst prepared in accordance with said Preparation Example of Solid Catalyst and composed of spherical α-alumina particles with a particle diameter of 5 mm and 0.5% by weight of palladium and 0.13% by weight of iron (calculated as metals) [Fe/Pd atomic ratio=0.5] deposited thereon. A starting gaseous mixture comprising 10% by volume of methyl nitrite, 20% by volume of carbon monoxide, 3% by volume of nitrogen monoxide, 5% by volume of methanol and 57% by volume of nitrogen was passed through the catalyst layer at a flow rate of 3,000 liters/hr (S.T.P.). The continuous reaction was conducted at a reaction temperature of 100° C. and a reaction pressure of 3 kg/cm²G.

As a result, the space time yield of dimethyl oxalate was 490 g/liter.hr after 100 hours from the initiation of the reaction and 320 g/liter.hr after 2,000 hours from the initiation of the reaction.

EXAMPLE 8

The procedure of Example 1 was followed except that a gaseous mixture comprising 5% by volume of ethyl nitrite, 20% by volume of carbon monoxide and 75% by volume of nitrogen was used and SV (space velosity; S.T.P.) was set at 5,000 hr$^{-1}$. In consequence, the space time yield of diethyl oxalate in the initiation of the reaction was 479 g/liter.hr, and the ratio of the space time yield was approximately the same as that in Example 1. With respect to the selectivity based on CO in the initiation of the reaction, diethyl oxalate was 98.0%, diethyl carbonate was 2.0% and byproduct $CO_2$ was slight.

EXAMPLE 9

A spherical solid catalyst (Fe/Pd atomic ratio=1) composed of α-alumina and 0.5% by weight of palladium and 0.262% by weight of iron (calculated as metals) deposited thereon was produced in accordance with said Preparation Example of Solid Catalyst except that the reduction temperature in the hydrogen stream was changed to 700° C.

The procedure of Example 1 was followed except using 2 ml of the above catalyst.

As a result, the space time yield of dimethyl oxalate in the initiation of the reaction was 1331 g/liter. hr and the decrease of the space time yield was little observed even after the reaction of 1000 hours.

What is claimed is:

1. In a process for preparing a diester of oxalic acid by the vapor phase catalytic reaction of carbon monoxide with an ester of nitrous acid in the presence of a catalyst composed of a solid carrier and a catalyst component supported on the carrier, the improvement wherein said catalyst component is composed of
   (a) a platinum-group metal or a salt thereof in an amount of from about 0.01 to about 10% by weight, calculated as the platinum-group metal, based on the weight of the carrier, and
   (b) at least one number selected from the group consisting of iron and an iron (II or III) compound, the atomic ratio of the component (a) to the component
   (b) as metal being from 10,000:1 to 1:4.

2. The process of claim 1 wherein the atomic ratio of the component (a) to the component (b) as metal is 5,000:1 to 1:3.
3. The process of claim 1 wherein said ester of nitrous acid is an ester of nitrous acid with an alcohol having 1 to 8 carbon atoms selected from the group consisting of saturated monohydric aliphatic alcohols and alicyclic alcohols.
4. The process of claim 1 wherein the catalytic reaction is carried out at a temperature of about 50° C. to about 200° C.
5. The process of claim 1 wherein the catalytic reaction is carried out at a pressure ranging from atmospheric pressure to about 10 kg/cm$^2$G.
6. The process of claim 1 wherein the amount of the component (a) supported is about 0.1 to about 2% by weight calculated as the platinum-group metal based on the weight of the carrier.
7. The process of claim 1 wherein said catalyst is prepared by impregnating the solid carrier with an aqueous solution of a water-soluble salt of the platinum-group metal and an aqueous solution of a water-soluble salt of iron, treating and impregnated solid carrier with an alkali, and then subjecting the alkali-treated product to reducing treatment in the liquid or gaseous phase.
8. The process of claim 7 wherein said alkali is selected from the group consisting of hydroxides, carbonates and bicarbonates of alkali metals or alkaline earth metals.
9. The process of claim 1 wherein the solid carrier is activated carbon, alumina, silica, diatomaceous earth, silicon carbide, pumice, zeolite or molecular sieve.
10. The process of claim 1 wherein the solid carrier is α-alumina, γ-alumina, silica or silicon carbide.
11. The process of claim 2 wherein the amount of the component (a) supported is about 0.1 to about 2% by weight calculated as the platinum-group metal based on the weight of the carrier.
12. The process of claim 1 wherein the component (a) comprises palladium or a salt thereof.
13. The process of claim 2 wherein the component (a) comprises palladium or a salt thereof.
14. The process of claim 6 wherein the component (a) comprises palladium or a salt thereof.
15. The process of claim 1 wherein component (b) is selected from the group consisting of metallic iron, ferrous sulfate, ferric sulfate, ferrous nitrate, ferric nitrate, ferrous chloride, ferric chloride, ammonium ferrous sulfate, ammonium ferric sulfate, ferrous citrate, ferrous lactate, ferric lactate, ferrous oxide, ferric oxide, tri-iron tetroxide, ferrous hydroxide, ferric hydroxide and mixtures thereof.

* * * * *

UNITED STATES PATENT AND TRADEMARK OFFICE
CERTIFICATE OF CORRECTION

PATENT NO. : 4,874,888
DATED : October 17, 1989
INVENTOR(S) : Yasushi Shiomi; Tokuo Matsuzaki; Katsuro Masunaga It is certified that error appears in the above-identified patent and that said Letters Patent is hereby corrected as shown below:

Claim 7, line 5, delete "and", and insert therefor --the--.

Signed and Sealed this

Thirtieth Day of October, 1990

Attest:

HARRY F. MANBECK, JR.

*Attesting Officer*    *Commissioner of Patents and Trademarks*